United States Patent [19]

Sundh

[11] Patent Number: 5,753,830

[45] Date of Patent: May 19, 1998

[54] METHOD AND SYSTEM FOR SAMPLING IN A MATERIAL MIXTURE

[75] Inventor: Göran Sundh, Sundsvall, Sweden

[73] Assignee: Sunds Defibrator Industries AB, Sweden

[21] Appl. No.: 687,378

[22] PCT Filed: Jan. 30, 1995

[86] PCT No.: PCT/SE95/00083

§ 371 Date: Aug. 5, 1996

§ 102(e) Date: Aug. 5, 1996

[87] PCT Pub. No.: WO95/23327

PCT Pub. Date: Aug. 31, 1995

[30] Foreign Application Priority Data

Feb. 28, 1994 [SE] Sweden ............ 9400687

[51] Int. Cl.[6] ............................. G01N 1/10
[52] U.S. Cl. .................. 73/863.83; 73/863.81; 73/864.81; 73/64.56
[58] Field of Search ............ 73/23.2, 23.41, 73/23.42, 64.56, 863, 863.41, 863.43, 863.51, 863.53, 863.58, 863.81, 863.83, 863.57, 864.81, 863.82

[56] References Cited

U.S. PATENT DOCUMENTS

| | | |
|---|---|---|
| 3,765,226 | 10/1973 | Strickland et al. . |
| 4,198,862 | 4/1980 | Rubin . |
| 4,594,903 | 6/1986 | Johnson . |
| 4,635,470 | 1/1987 | Skållen et al. . |
| 4,908,676 | 3/1990 | Bedell et al. .......... 73/61.52 |
| 4,974,455 | 12/1990 | McGowan et al. .......... 73/863.81 |
| 5,109,708 | 5/1992 | Lawless .......... 73/863.83 |
| 5,345,828 | 9/1994 | Peterson .......... 73/863.57 |
| 5,423,228 | 6/1995 | Budd et al. .......... 73/863.81 |

FOREIGN PATENT DOCUMENTS 0 430 021 A2  6/1991  European Pat. Off. .

*Primary Examiner*—Hezron E. Williams
*Assistant Examiner*—Nashmiya Fayyaz
*Attorney, Agent, or Firm*—Lerner, David, Littenberg, Krumholz & Mentlik

[57] ABSTRACT

Methods for sampling mixtures of flowable materials such as pulp streams are disclosed including tapping a minor portion of these mixtures and circulating the tapped portion continuously through a circuit, diluting the circulating tapped mixture to dilute the tapped mixture to a predetermined concentration, and recycling a portion of the diluted stream to the original mixture of materials. Apparatus for carrying out such a method is also disclosed.

5 Claims, 1 Drawing Sheet

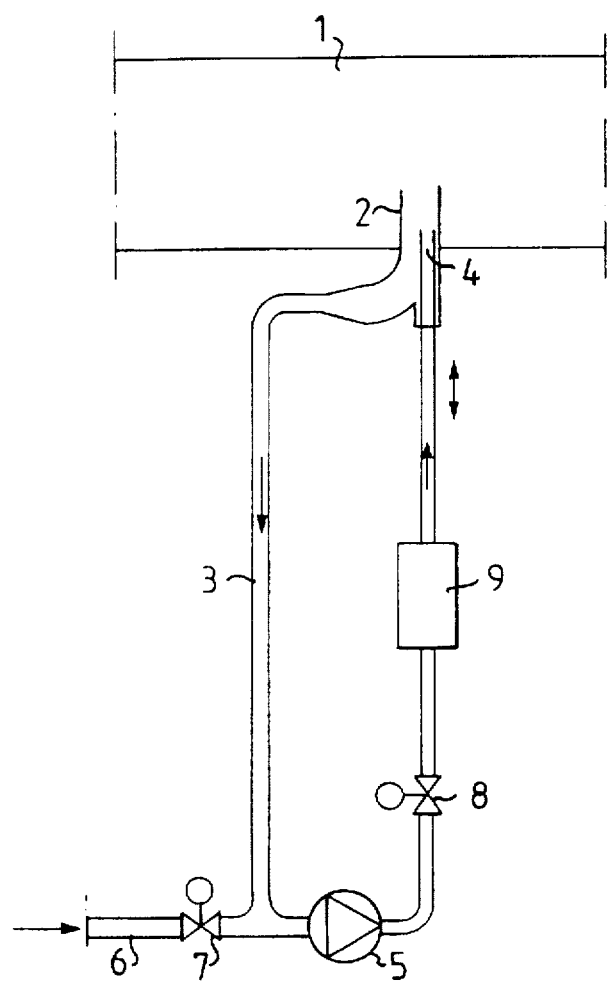

5,753,830

METHOD AND SYSTEM FOR SAMPLING IN A MATERIAL MIXTURE

FIELD OF THE INVENTION

The present invention relates to a method and system for continuous sampling of material mixtures for the purpose of analyzing same. Examples of such material mixtures are particles contained in a liquid, such as fiber suspensions, such as papermaking pulps. The present invention, however, can also be applied to other mixtures of particles, liquids and gases. The sampling can be carried out from a space, for example a conveying pipe, or from a tank holding the material mixture.

BACKGROUND OF THE INVENTION

During analysis of the properties of papermaking pulp it is normally of great importance to obtain accurate measuring results, thus requiring that the concentration be both constant and known. Examples of such properties which are to be analyzed are the content of various impurities, the shives content, dewatering capacity (freeness), and fiber appearance and properties.

Certain analytical methods require very low concentrations compared with the normal pulp concentration in the process. One example thereof is image analysis of fiber properties, where the dilution demand can be 1:1000 or even higher.

During continuous sampling this has made it necessary to employ very long conveying times thereby delaying the measuring results or requiring a large consumption of clean dilution water. One method of successfully dealing with these problems would be to reduce the pipe diameter in the sampling equipment. This possibility, however, is restricted by the risk of plugging, especially when both the concentration and the dilution demand are high at the same time.

Additional problems arise due to the fact that the sample taken, besides being diluted, must also be mixed to a uniform concentration before it can be analyzed.

SUMMARY OF THE INVENTION

In accordance with the present invention, these and other problems have now been solved by the invention of a method for sampling a mixture of flowable materials which comprises tapping a minor portion of the mixture, circulating the tapped portion of the mixture continuously through a circuit, diluting the circulating tapped portion of the mixture in order to dilute the tapped portion to provide a diluted stream having a predetermined concentration, and recycling a portion of the diluted stream to the mixture of flowable materials.

In accordance with one embodiment of the method of the present invention, recycling of a portion of the diluted stream comprises adjustably recycling the predetermined portion of the diluted stream to the mixture of flowable materials.

In accordance with another embodiment of the method of the present invention, the method includes continuously measuring the predetermined concentration and controlling the diluting of the circulating tapped portion of the mixture based thereon.

In accordance with the apparatus of the present invention, apparatus is provided for sampling a mixture of flowable materials comprising a sample receiving tap for tapping a minor portion of the mixture, a circuit for continuously circulating the tapped portion of the mixture from the sample receiving tap to an exit point associated with the sample receiving tap, a pump for pumping the tapped portion of the mixture through the circuit, and dilution feed means for controllably feeding a dilution liquid into in order to dilute the tapped portion of the mixture to provide a diluted stream having a predetermined concentration at the exit point.

In accordance with one embodiment of the apparatus of the present invention, the apparatus includes a sample analyzer for analyzing the diluted stream in the circuit.

In accordance with another embodiment of the apparatus of the present invention, the exit point is adjustably located with respect to the sample receiving tap.

In accordance with another embodiment of the apparatus of the present invention, the apparatus includes valve means in the circuit for controlling the flow of the tapped portion of the mixture in the circuit.

In accordance with the present invention, a solution is provided to the above-noted problems in which a portion of the material mixture is directed in a continuous flow into a pipe coil while simultaneously being diluted to a desired concentration for analysis, and at the same time an adjustable portion of this flow is recycled to the material mixture itself.

The partial recirculation in the coil thus yields a high dilution factor at a small dilution liquid flow, at the same time as the flow in the coil can be high, thereby causing only a short delay in conveying.

The risk of plugging is also small, since the concentration in the entire coil is low, and the net flow runs form the coil into the material mixture.

BRIEF DESCRIPTION OF THE DRAWING

The present invention may be more fully appreciated with reference to the following detailed description, which in turn refers to the FIGURE which shows a schematic representation of an embodiment of the present invention.

DETAILED DESCRIPTION

Referring to the FIGURE, a material mixture, for example a pulp suspension, in a process pipe is to be analyzed. A sample tapping point 2 communicates with the pipe 1 for diverting a portion of the pulp, and is connected to the pipe. This tapping point 2 is preferably formed as a short pipe extending some distance into the pipe 1, so that the sample shall be representative, and furthermore so that corner effects during the analysis can be avoided. The tapping point 2 is connected to a pipe coil 3, the other end of which 4 opens at the tapping point 2. The pipe coil 3 comprises a pump 5 for circulating the sample taken in the coil. A feed pipe 6 for dilution liquid, is connected to the pipe coil 3. A valve 7 controls the supply of dilution liquid so as to vary and control the concentration in the coil, which is measured continuously.

The pump 5 can be, for example, a simple centrifugal pump, which sucks in a portion of the pulp from the pipe 1 and causes it to circulate and be mixed to a uniform concentration in the pipe coil 3. The flow in the pipe coil is thus determined by the pump 5, but can also be controlled by means of a valve 8 in the pipe coil.

The mouth 4 of the pipe coil 3 at the sample tapping point 2 is preferably adjustable, for determining the reflux to the pipe 1. Depending on the configuration and location of the sample tapping point 2 and mouth 4 in relation to each other, the yield, that is, the tapped pulp and its recirculation can vary from no yield at all, i.e. merely recirculation in the pipe coil, to complete yield, i.e. no recirculation in the pipe coil. The degree of yield, i.e. the amount of new pulp supplied to the pipe coil, can also be controlled by the flow rate in the coil.

It is possible to calculating the degree of yield, as it is in direct relation to the concentration in the coil and the dilution liquid flow, when the system is in balance.

In the embodiment shown in the FIGURE, the mouth 4 of the pipe coil is vertically adjustable. It extends upward in the sample tapping point 2 and is located immediately below the opening of the sample tapping point in the pipe 1. Alternatively, the adjustable mouth 4 can be directed downward from above to the sample tapping point 2 and can be raised or lowered or be laterally movable above the edge of the sample tapping point 2. The mouth can also be directed obliquely in relation to the sample tapping point 2.

Owing to the adjustability of the mouth 4 in relation to the sample tapping point 2, as described above, the yield, i.e. the amount of new material mixture supplied to the pipe coil 3, can be adjusted.

The analysis of the material mixture can be carried out anywhere in the pipe coil, but preferably takes place immediately after the pump. The analysis equipment 9 can be of a type known per se for measuring different properties of the material mixture. The properties of a pulp suspension are to be analyzed with different meters at different concentrations. The impurities content, for example, can be measured at a pulp concentration of about 1%, the freeness at about 0.3%, the shives content at about 0.01%, and the fiber appearance at about 0.0005%. As it is desired to carry out the measurings approximately simultaneously, it is necessary to rapidly change the concentration in the pipe coil, which is possible with the controls and adjustments described above.

For analyses to be carried out batchwise, for example, to analyze the freeness measuring of a pulp suspension, a portion of the content in the coil is diverted into an analyzer and locked in for analysis. The sample is then recycled to the material mixture or discharged.

When the sample tapping point 2 is connected to a sampling tank instead of to a pipe, analyses which cannot be made directly in a flow of the material mixture are made batchwise, for example samples supplied batchwise to a sampling tank of a pulp suspension.

The sampling equipment according to the present invention can also be controlled and utilized for the control and calibration of analyzers by connecting the sample tapping point to a vessel containing a material mixture with known properties.

Owing to the fact that the sampling system according to the present invention renders it possible to adjust the desired concentration for analysis very rapidly, the length of the pipe coil is not critical, but the place of analysis can be located at a distance form the sample tapping point when this is preferred in view of local conditions.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A method for sampling a mixture of flowable materials comprising tapping a minor portion of said mixture through a sample receiving tap to form a tapped portion, circulating said tapped portion of said mixture through a circuit, diluting said circulating tapped portion of said mixture in said circuit in order to provide a diluted stream having a predetermined concentration, recirculating a first portion of said diluted stream through said circuit, adjusting a location of a circuit exit point within said sample receiving tap to control an amount of said diluted stream that is recirculated; and continuously recycling a remaining portion of said diluted stream to said mixture of flowable materials.

2. The method of claim 1 including continuously measuring a concentration of said diluted stream to obtain concentration measurements and controlling said diluting of said circulating tapped portion of said mixture based on said measurements.

3. Apparatus for sampling a mixture of flowable materials comprising a sample receiving tap for tapping a minor portion of said mixture, a circuit for continuously circulating said tapped portion of said mixture from said sample receiving tap to an exit point adjustably located within said sample receiving tap to control an amount of said diluted stream recycled to said flowable mixture, a pump for pumping said tapped portion of said mixture through said circuit, and dilution feed means for controllably feeding a dilution liquid into said circuit in order to dilute said tapped portion of said mixture to provide a diluted stream having a predetermined concentration at said exit point.

4. The apparatus of claim 3 including a sample analyzer for analyzing said diluted stream in said circuit.

5. The apparatus of claim 3 including valve means in said circuit for controlling the flow of said tapped portion of said mixture in said circuit.

* * * * *